(12) United States Patent
Emonds-Alt et al.

(10) Patent No.: US 7,390,823 B2
(45) Date of Patent: Jun. 24, 2008

(54) USE OF SAREDUTANT AND OF ITS PHARMACEUTICALLY ACCEPTABLE SALTS FOR THE PREPARATION OF MEDICINAL PRODUCTS THAT ARE USEFUL IN THE TREATMENT OR PREVENTION OF ALL MOOD DISORDERS, ADAPTATION DISORDERS OR MIXED ANXIETY-DEPRESSION DISORDERS

(75) Inventors: Xavier Emonds-Alt, Combaillaux (FR); Philippe Soubrie, Valflaunes (FR); Régis Steinberg, Prades le Lez (FR)

(73) Assignee: Sanofi-Aventis, Paris (FR)

( * ) Notice: Subject to any disclaimer, the term of this patent is extended or adjusted under 35 U.S.C. 154(b) by 479 days.

(21) Appl. No.: 10/409,504

(22) Filed: Apr. 8, 2003

(65) Prior Publication Data

US 2003/0176462 A1 Sep. 18, 2003

Related U.S. Application Data

(63) Continuation of application No. 09/958,439, filed as application No. PCT/FR00/01084 on Apr. 25, 2000, now Pat. No. 6,573,281.

(30) Foreign Application Priority Data

Apr. 27, 1999 (FR) .................................. 99 05338

(51) Int. Cl.
*A61K 31/445* (2006.01)

(52) U.S. Cl. ........................................ 514/329; 514/317

(58) Field of Classification Search ................. 514/329
See application file for complete search history.

(56) References Cited

U.S. PATENT DOCUMENTS

| 5,236,921 | A | * | 8/1993 | Emonds-Ai et al. .... 514/252.14 |
| 5,554,644 | A | | 9/1996 | Horwell et al. |
| 5,691,336 | A | * | 11/1997 | Dorn et al. ............... 514/236.2 |
| 6,177,450 | B1 | | 1/2001 | Garret et al. |
| 6,573,281 | B1 | * | 6/2003 | Emonds-Alt et al. ........ 514/329 |

FOREIGN PATENT DOCUMENTS

WO 94/16697 8/1994

OTHER PUBLICATIONS

The Merck Manual, Section 15, Chapter 189,http://www.merck.com/mrkshared/mmanual/section15/chapter189/189a.jsp.*
http://fly.hiwaay.net/~garson/alone.htm Brochure from the U.S. Dept of Health and Human Services, Public Health Service, National Institute of Mental Health DHHS Publication No. (ADM)92-1178, Prented 1990, Revised 1992.*
Walsh et al., The Anxiolytic-like activity of GR159897, a non-peptide NK2 receptor antagonist, in rodent and primate models of anxiety, Psychopharmacology (1995) 121: 186-191.*
Rouillon, Anxiety with depression: a treatment need. (1999) European Neuropsychopharmacology 9 Suppl. 3 S87-S92.*
Teixiera et al., Effects of Cental administration of tachykinin receptor agonists and antagonists on plus-maze behaviour in mice. European Journal of Pharmacology (1996) 311 pp. 7-14.*
Phillips, Tamara J. (principal investigator), Genetic Determinants of Drug Effects, Sponsoring Org, Dept. of Veteran Affairs, Identifying No. 109201 Oct. 1, 1994.*
Hagan et al., Vineyard Peptide Conference Bears Fruit, TiPS, (14), p. 315-318, (1993).
Teixeira, et al., Effects of Central Administration of Tachykinin Receptor Agonists and Antagonists on Plus-Maze Behavior in Mice, European Journal of Pharmacology, 311, pp. 7-14 (1996).
Khawaja et al., Tachykinins: Receptor to Effector, Int. J. Biochem. Cell. Biol., 28(7), pp. 721-738 (1996).
Culman et al., Effect of Tachykinin Receptor Inhibition in the Brain on Cardiovascular & Behavioral Responses to Stress, The Journal of Pharmacology & Experimental Therapeutics, 280(1), pp. 238-246 (1997).
Ikeda et al., RP67580, A Neurokinin1 Receptor Antagonist, Decreased Restraint Stress-Induced Defecation in Rat, Neuroscience Letters, 198, pp. 103-106 (1995).

* cited by examiner

*Primary Examiner*—Ardin Marschel
*Assistant Examiner*—Donna Jagoe
(74) *Attorney, Agent, or Firm*—Balaram Gupta

(57) ABSTRACT

The present invention relates to the use of saredutant and of its pharmaceutically acceptable salts for the preparation of medicinal products that are useful in the treatment or prevention of all mood disorders, adaptation disorders or mixed anxiety-depression disorders.

1 Claim, No Drawings

USE OF SAREDUTANT AND OF ITS PHARMACEUTICALLY ACCEPTABLE SALTS FOR THE PREPARATION OF MEDICINAL PRODUCTS THAT ARE USEFUL IN THE TREATMENT OR PREVENTION OF ALL MOOD DISORDERS, ADAPTATION DISORDERS OR MIXED ANXIETY-DEPRESSION DISORDERS

CROSS REFERENCE TO RELATED APPLICATIONS

This application is a continuation of prior application Ser. No. 09/958,439 filed October 9, 2001 now U.S. Pat. No. 6,573,281, which in turn is a 35 U.S.C. §371 application of PCT International application No. PCT/FR00/01084, filed Apr. 25, 2000, which in turn claims priority from French Application No. 99/05338, filed Apr. 27, 1999.

The present invention relates to a novel use of saredutant.

Saredutant is the International Nonproprietary Name (I.N.N.) for (S)-(–)-N-methyl-N-[4-(4-acetylamino-4-phenylpiperid-1-yl)-2-(3,4-dichloro-phenyl)butyl]benzamide, of formula:

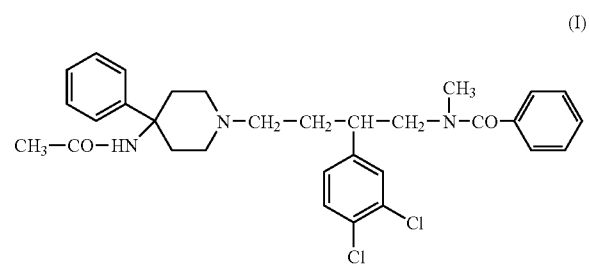

(I)

This compound and its pharmaceutically acceptable salts are described in patent EP 0 474 561 B1 and in patent U.S. Pat. No. 5,236,921.

These compounds are described as antagonists of neurokinin A receptors and may be useful in any neurokinin A-dependent pathology and more particularly in neurogenic inflammations of the respiratory pathways. These compounds have also been described as powerful and selective non-peptide antagonists of the $NK_2$ receptors of neurokinin A (Life Sciences, 1992, 50 (15), PL101-PL106).

It has now been found that saredutant and its pharmaceutically acceptable salts are useful in the treatment or prevention of all mood disorders, adaptation disorders and mixed anxiety-depression disorders, whether or not these disorders are induced by events of life or stressful events. The expression "mood disorder" means major depressive disorders, dysthymic disorders or bipolar disorders.

Thus, according to one of its aspects, a subject of the present invention is the use of saredutant and of its pharmaceutically acceptable salts for the preparation of medicinal products that are useful in the treatment or prevention of all mood disorders, adaptation disorders or mixed anxiety-depression disorders.

In particular, a subject of the present invention is the use of saredutant and of its pharmaceutically acceptable salts for the preparation of medicinal products that are useful in the treatment or prevention of all mood disorders, more particularly of major depressive disorders, dysthymic disorders or bipolar disorders.

In particular also, a subject of the present invention is the use of saredutant and of its pharmaceutically acceptable salts for the preparation of medicinal products that are useful in the treatment or prevention of adaptation disorders.

Finally, in particular, a subject of the present invention is the use of saredutant and of its pharmaceutically acceptable salts for the preparation of medicinal products that are useful in the treatment or prevention of mixed anxiety-depression disorders.

According to another of its aspects, a subject of the present invention is a method for treating or preventing all mood disorders, adaptation disorders or mixed anxiety-depression disorders by administration of a suitable dose of saredutant or of one of its pharmaceutically acceptable salts.

Saredutant and its pharmaceutically acceptable salts are prepared according to the process described in patent EP 0 474 561 B1 or that described in patent EP 0 698 601 B1.

The salts of the compound of formula (I) are the salts with conventional pharmaceutically acceptable inorganic or organic acids, such as the hydrochloride, hydrobromide, sulphate, hydrogen sulphate, dihydrogen phosphate, methanesulphonate, methyl sulphate, acetate, oxalate, maleate, fumarate, succinate, 2-naphthalene-sulphonate, glyconate, gluconate, citrate, isethionate, benzenesulphonate or para-toluenesulphonate.

For their use as medicinal products, the compound of formula (I) and its pharmaceutically acceptable salts are generally administered in dosage units. The said dosage units are preferably formulated in pharmaceutical compositions in which the active principle is mixed with a pharmaceutical excipient.

In the pharmaceutical compositions of the present invention for oral, sublingual, inhaled, subcutaneous, intramuscular, intravenous, transdermal, local or rectal administration, the active principle, alone or in combination with another active principle, can be administered in unit administration form, mixed with conventional pharmaceutical supports, to animals and to human beings. The appropriate unit administration forms comprise oral forms such as tablets, gel capsules, powders, granules and oral solutions or suspensions, sublingual and buccal administration forms, aerosols, topical administration forms, implants, subcutaneous, transdermal, intramuscular, intravenous or intranasal administration forms and rectal administration forms.

The daily dose of the compound of formula (I) is from 0.05 to 5 mg/kg, advantageously from 1 to 2.5 mg/kg, preferably from 2 to 2.5 mg/kg, to be administered in one or more dosage intakes. The compound of formula (I) and its salts are generally formulated in a dosage unit containing from 2.5 to 500 mg, advantageously from 50 to 250 mg and preferably from 100 to 250 mg, of active principle per dosage unit, to be administered in one, two or more dosage intakes at the same time, according to need. Although these doses are examples of average situations, there may be special cases in which higher or lower doses are appropriate, and such doses also form part of the invention. According to usual practice, the dose which is appropriate for each patient is determined by the doctor according to the mode of administration, the age, the weight and the response of the said patient.

When a solid composition in tablet form is prepared, a pharmaceutical vehicle is added to the micronized or non-micronized active principle, which vehicle can be composed of diluents such as, for example, lactose, microcrystalline cellulose, starch and formulation additives such as binders (polyvinylpyrrolidone, hydroxypropylmethylcellulose, etc.), flow agents such as silica, lubricants such as magnesium stearate, stearic acid, glyceryl tribehenate or sodium stearylfumarate.

Wetting agents or surfactants such as sodium lauryl sulphate can be added to the formulation.

The tablets can be prepared by various techniques: direct tabletting, dry granulation, wet granulation, hot melting.

The tablets can be plain or sugar-coated (for example coated with sucrose) or coated with various polymers or other suitable materials.

The tablets can undergo immediate, delayed or sustained release by preparing polymer matrices or by using specific polymers in the film-coating operation.

A preparation as a gel capsule is obtained by simply mixing the active principle with dry pharmaceutical vehicles (simple mixing or dry granulation, wet granulation or hot melting), liquid or semi-solid pharmaceutical vehicles.

The gel capsules can be soft or hard, and film-coated or otherwise, so as to have immediate, sustained or delayed activity (for example via an enteric form).

A preparation in syrup or elixir form can contain the active principle together with a sweetener, preferably a calorie-free sweetener, methylparaben and propylparaben as antiseptic, as well as a flavour enhancer and a suitable colorant.

The water-dispersible powders or granules can contain the active principle as a mixture with dispersing agents, wetting agents or suspending agents, such as polyvinylpyrrolidone, as well as with sweeteners or flavour enhancers.

For rectal administration, use is made of suppositories which are prepared with binders that melt at the rectal temperature, for example cocoa butter or polyethylene glycols.

For parenteral or intranasal administration, aqueous suspensions, isotonic saline solutions or sterile, injectable solutions which contain pharmacologically compatible dispersing agents and/or solubilizing agents, for example propylene glycol or butylene glycol, are used.

Thus, to prepare an aqueous solution for intravenous injection, it is possible to use a co-solvent such as, for example, an alcohol such as ethanol or a glycol such as polyethylene glycol or propylene glycol, and a hydrophilic surfactant such as Tween® 80. To prepare an oily solution for intramuscular injection, the active principle can be dissolved with a triglyceride or a glycerol ester.

For local administration, creams, ointments, gels or eye drops can be used.

For transdermal administration, patches can be used in multilayer or reservoir form in which the active principle can be in alcoholic solution.

For administration by inhalation, an aerosol is used containing, for example, sorbitan trioleate or oleic acid as well as trichlorofluoromethane, dichlorofluoromethane, dichlorotetrafluoroethane or any other biologically compatible propellent gas; a system containing the active principle alone or combined with an excipient, in powder form, can also be used.

The active principle can also be in the form of a complex with a cyclodextrin, for example, α-, β-, or γ-cyclodextrin, 2-hydroxypropyl-β-cyclodextrin or methyl-β-cyclodextrin.

The active principle can also be formulated in the form of microcapsules or microspheres, optionally with one or more supports or additives.

Among the sustained-release forms which are useful in the case of chronic treatments, implants can be used. These can be prepared in the form of an oily suspension or in the form of a suspension of microspheres in an isotonic medium.

According to the present invention, the oral administration forms are preferred.

The effect of saredutant on major depressive disorders is studied on patients aged from 18 to 65 years old. The patients receive saredutant orally (300 mg/day) for a period of about six weeks.

The improvement in the depressive syndromes is measured by means of a significant decrease in the scores on the Hamilton depression rating scale (HAM-D) as well as by the impressions received by the clinician and the patient's overall impressions. The Hamilton depression rating scale is defined by M. Hamilton in J. Neurol. Neurosurg. Psychiat., 1960, 23, 56-62.

In the examples which follow, saredutant is used in monosuccinate form.

| EXAMPLE 1: Gel capsule containing 25 mg of saredutant. | | |
| --- | --- | --- |
| saredutant (expressed as base) | | 25.0 mg |
| lactose monohydrate (200 mesh) | qs | 170 mg |
| croscarmellose sodium | | 3.4 mg |
| magnesium stearate | | 1.7 mg |
| purified water* | qs | |
| for an opaque white size 3 gel capsule, filled to | | 170 mg |

*evaporated off on drying after the wet granulation.

| EXAMPLE 2: Gel capsule containing 100 mg of saredutant. | | |
| --- | --- | --- |
| saredutant (expressed as base) | | 100.0 mg |
| lactose monohydrate (200 mesh) | qs | 170 mg |
| croscarmellose sodium | | 3.4 mg |
| magnesium stearate | | 1.7 mg |
| purified water* | qs | |
| for an opaque white size 3 gel capsule, filled to | | 170 mg |

*evaporated off on drying after the wet granulation.

The invention claimed is:

1. A method for the treatment of major depressive disorders which comprises administering to a patient in need of such treatment an effective amount of saredutant or a pharmaceutically acceptable salt thereof.

* * * * *